United States Patent [19]

Re et al.

[11] Patent Number: 4,851,485
[45] Date of Patent: Jul. 25, 1989

[54] FLUORINATED CROSS-LINKING AGENTS FOR EPOXY RESINS AND PROCESS FOR PREPARING THE RESINS

[75] Inventors: Alberto Re; Claudio Tonelli; Vito Tortelli, all of Milan, Italy

[73] Assignee: Ausimont S.p.A., Milan, Italy

[21] Appl. No.: 201,091

[22] Filed: Jun. 1, 1988

[30] Foreign Application Priority Data

Jun. 2, 1987 [IT] Italy ................ 20747 A/87

[51] Int. Cl.$^4$ .............. C08G 59/40; C08G 59/42; C08G 18/00
[52] U.S. Cl. .................... 525/504; 525/505; 525/507; 528/70; 528/109; 528/110; 528/112; 528/121; 528/365; 528/374; 528/401
[58] Field of Search ............ 528/70, 110, 112, 109, 528/121, 365, 374, 401; 525/504, 505, 507

[56] References Cited

U.S. PATENT DOCUMENTS

| | | | |
|---|---|---|---|
| 3,458,571 | 7/1969 | Tokoli | 528/121 X |
| 4,284,746 | 8/1981 | Ohmori | 528/121 X |
| 4,699,969 | 10/1987 | Re et al. | 528/401 X |

*Primary Examiner*—Earl Nielsen
*Attorney, Agent, or Firm*—Stevens, Davis, Miller & Mosher

[57] ABSTRACT

Non-fluorinated epoxy resins of a known type are cross-linked by means of polyfunctional fluoroalkanes containing groups which are reactive with the epoxy groups and/or with the hydroxy groups present in the starting resin. The cross-linked products so obtained, having a fluorine content not higher than 15% by weight, and preferably ranging from 1% to 5%, exhibit a complex of properties which are typical of the corresponding fluorinated resins having a much higher fluorine content; in particular, oil- and water-repellency, resistance to hydrolysis and to solvents, and minimum absorption of water.

6 Claims, No Drawings

FLUORINATED CROSS-LINKING AGENTS FOR EPOXY RESINS AND PROCESS FOR PREPARING THE RESINS

DESCRIPTION OF THE INVENTION

The present invention involves the cross-linking of non-fluorinated epoxy resins of a known type, with fluorinated polyfunctional cross-linking agents characterized by a chain of fluoroalkylene units, in order to obtain cross-linked resins having improved properties with respect to the corresponding resins of known type not containing fluorine.

The specific characteristics of the cross-linked resins obtained according to this invention are:
surface properties which impart oil- and water-repellency and a low coefficient of friction to the product;
resistance to hydrolysis and minimum absorption of water
resistance to solvents;
advantageous dielectric characteristics, in particular as regards dielectric constant and volume resistivity.

The present invention is based on the surprising fact that, starting from a non-fluorinated epoxy resin and cross-linking said resin with a polyfunctional fluoroalkane it is possible to obtain a cross-linked product having the typical characteristics of a cross-linked epoxy resin obtained starting from a fluorinated epoxy polymer.

The cross-linking process according to the invention provides cross-linked products which, although having a fluorine content not exceeding 15%, and preferably ranging from 1% to 5% by weight, exhibit the same typical surface fluorine content, which gives rise to a high oil- and water-repellency, a minimum absorption of water, and a high resistance to hydrolysis and to solvents.

As starting epoxy resins there may be cited:
Epoxy resins from bisphenol A - epichlorohydrin:

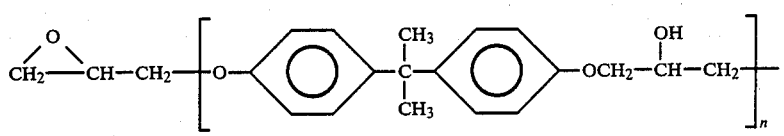

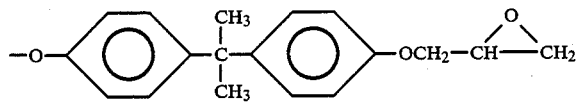

Epoxy cresol novolak resins:

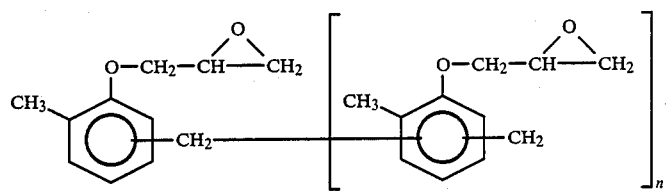

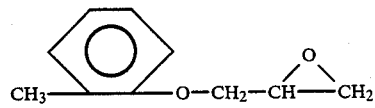

Epoxy phenolic novolak resins:

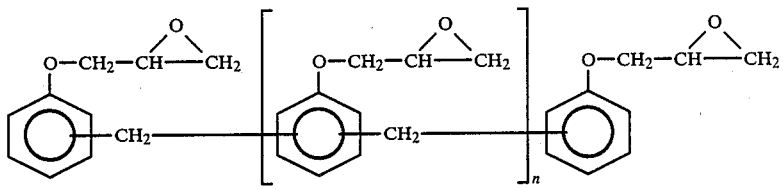

Resins from bisphenol F:

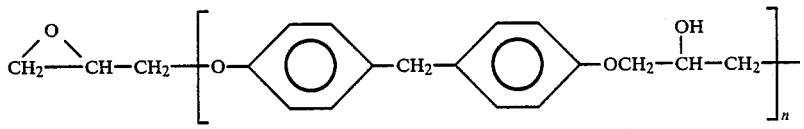

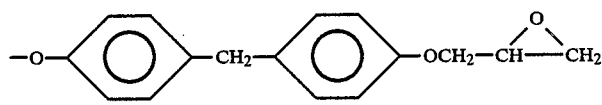

In the above formulae, n has a value ranging over wide limits, from 1 up to 10 and even above (see Kirk Othmer, Encyclopedia of Chemical Technology, Vol. 8, Ed. 1967, page 300).

Polynuclear resins from phenol-glycidyl ether:

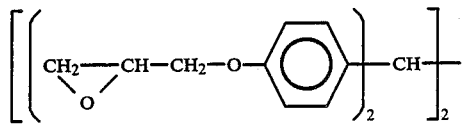

Resins from tetraglycidylmethylene dianiline:

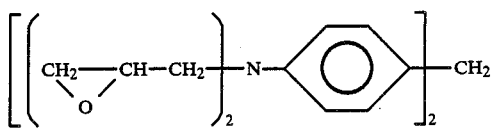

Resins from triglycidyl isocyanurate:

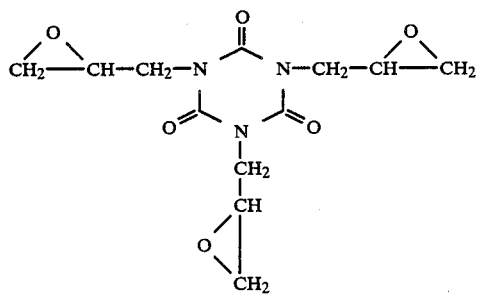

Resins from diglycidylhydantoin:

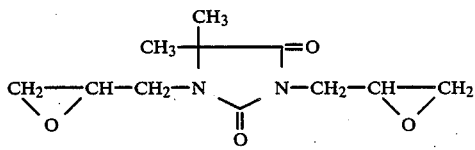

Resins from bisphenols or other halogenated monomers; for example, tetrabromobisphenol A and tetrachlorobisphenol A.

It is possible also to use mixtures of one or more of the above resins.

The cross-linking agent according to the present invention is a perfluoroalkane with straight or branched structure, having at both ends functional groups which are reactive with the starting epoxy resin and which are selected from:

NCO
NH$_2$
COOH
OH
SH
anhydride group
comprised in one of the following formulae:

$$A-(CF_2CF_2)_n-A' \quad (I)$$

$$A-(CF_2CF_2)_m(CF_2CF)_p-A' \quad (II)$$
$$\quad\quad\quad\quad\quad\quad\quad |$$
$$\quad\quad\quad\quad\quad\quad\quad CF_3$$

where n=2 to 8; m=1 to 8; p=0 to 6; m+p being at least 2; A and A' are end groups containing in the aggregate two or more than two of the functional groups mentioned above.

End groups A and A' generally contain, although not in all cases, a divalent radical W linking the functional group and the perfluoroalkylene chain.

The linking divalent radical W may be of the aliphatic, cycloaliphatic, aromatic or heterocyclic type. Linking groups are, for example:

(W.1)—$(CH_2)_m$—, where m=1 or 2;

$$-CH_2CH-,$$
$$\quad\quad |$$
$$\quad\quad Q$$

where Q is a $C_1$-$C_3$ alkyl or a phenyl

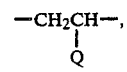

—$(CH_2)_m(OCH_2CH_2)_s$—, where s=1 to 8 and m=1 or 2; —$(CH_2)_m$ $$-(CH_2)_m\left(OCH_2\underset{\underset{CH_3}{|}}{CH}\right)_s-;$$

—$CHCH_3$—; —$OCH_2CH_2CH_2$—.

Group W may furthermore be selected (W.2) from the arylene radicals:

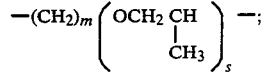

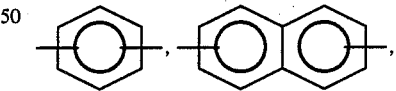

optionally containing also substituents on the ring, (W.3) or from heterocyclic radicals such as:

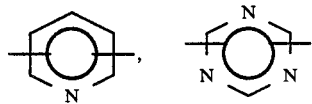

(W.4) or from polycyclic radicals such as:

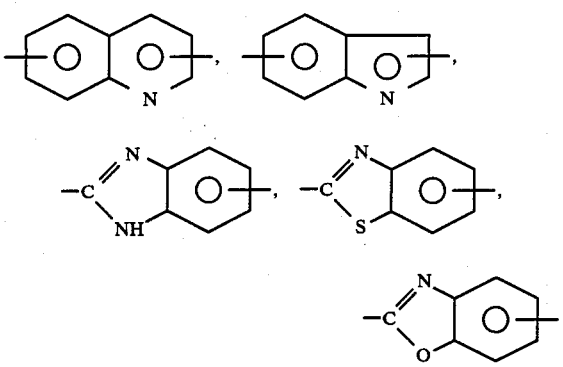

The linking groups of type W.2, W.3, and W.4 may be bound to the perfluoroalkylene chain either directly or through one or two —CH$_2$—groups.

The cross-linking agent may also have the functional groups on only one end of the perfluoroalkane chain, the other end group being free from functional groups.

As polyfunctional end groups, the following may be cited for example: —(CH$_2$CH$_2$OH)$_2$;

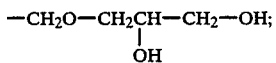

diisocyanates, 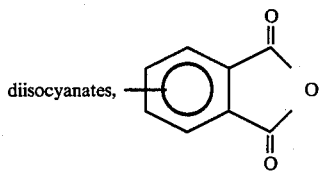

and other anhydride end groups susceptible to opening up of the ring under the reaction conditions.

The preparation of polyfunctional perfluoroalkanes to be used according to the present invention is described in particular in Italian patent applications Nos. 19779 A/86 and 19780 A/86.

When carrying into effect the present invention, the fluorinated cross-linking agent according to the invention may also be used in admixture with non-fluorinated cross-linking agents of a known type. This permits one to maintain the fluorine content within the above-indicated range.

The epoxy resins utilizable for the present invention may be liquid, solid or in solution, depending on the field of use. The liquid epoxy resins prevailingly contain epoxy groups and are cross-linked with reagents which contain active hydrogens, for example polyamines, polycarboxylic acids, polythiols, polyphenols, polyaminoamides, or the anhydride group, either with or without the presence of catalysts such as acids or Lewis bases, for example complexes of boron trifluoride or tertiary amines.

In accordance with the present invention, the liquid epoxy resins may be cross-linked with perfluoroalkane derivatives containing end groups such as, for example, NH$_2$, COOH, (CO)$_2$O, SH, as already mentioned above.

The cross-linking reaction may be conducted for example at room temperature (with a non-aromatic amine), or up to temperatures higher than 200° C. (with an anhydride).

Conventional techniques well known in the art for the cross-linking of epoxy resins with cross-linking agents are fully utilizable in the present invention.

The solid epoxy resins contain epoxy end groups and free hydroxy groups in the chain. Thus, in accordance with the present invention, they may be cross-linked with the above-indicated reagents, or by reaction with a fluoroalkane having an isocyanate end group. In this case, the reaction giving rise to the polyurethane bond may or may not be catalyzed by catalysts which, in general, are utilized in the technology of polyurethanes obtained from polyols and polyisocyanates. In any case, the addition of an efficacious catalyst system permits one to operate at low temperatures (20°–100° C.) and for short times. Furthermore, a proper amount of added catalyst permits one to optimize the pot life, i.e., the time during which the reaction mixture remains fluid.

As catalyst one may utilize tin derivatives such as dibutyl tin dilaurate, dibutyl tin diacetate, dibutyl tin oxide; iron derivatives such as iron acetylacetone; titanium alcoholates such as titanium tetraisopropylate; and tertiary amines such as triethylamine, the amounts ranging from 0.001 to 2% by weight referred to the total weight, and preferably from 0.01 to 0.5%.

Generally, the admixing of the fluorinated cross-linking agent does not create any particular problems. In some cases, hwoever, it is possible to facilitate the mixing by adding suitable solvents such as esters, for example butyl acetate and amyl acetate; ketones, for example methylethylketone and methylisobutylketone; and aromatic hydrocarbons, for example xylene and toluene.

The amount of solvent utilized depends on the viscosity desired for the solution.

The formulations of the epoxy resins prepared in accordance with the present invention may include other ingredients such as pigments or fillers of various nature, in relation to the requirements of the various applicative sectors, said ingredients having the purpose of reducing the cost of the manufactured articles and of increasing their consistency, of levelling the pigment within the resin, or of contributing to reinforcing the structure of the resin in mechanical respects.

The pigments and other fillers, either of a pigmentary nature of otherwise, may be added in order to coat and/or protect the surface on which the resin is spread, for example by reflecting the destroying rays of the sun, which otherwise could pass through the resin coating and cause a degradation of the underlying material.

The resins prepared from the polymers of this invention, although their fluorine content is low, are compatible with fillers of a particular nature, such as e.g., polytetrafluoroethylene (PTFE), and C$_2$F$_4$/C$_3$F$_6$ copolymers (FEP), which may be added to improve mechanical characteristics such as impact strength and abrasion resistance.

The use, in accordance with the present invention, of cross-linking agents having a fluoroalkane chain imparts to the conventional epoxy resins considerably improved chemicophysical and mechanical characteristics as compared with hydrogenated epoxy resins of the prior art, because said agents render the materials obtainable suitable for a wide variety of utilizations.

In particular, the resins obtainable according to the present invention are characterized by:
a high resistance to chemical agents, to hydrolysis and to atmospheric agents,
a high thermal resistance,
a considerable dimensional stability, self-lubricating properties,
a low wettability,
excellent mechanical properties,
water-repellency,
fat-repellency,
antiflame properties,
a low dielectric constant, and
a high thermal dissipation factor.

In consideration of such exceptional characteristics, some of the applicative sectors of the products of this invention are those of adhesives, structural materials, and high-performance composite materials, or, for example, in the sector of electronics, as supporting resins for printed circuits, encapsulating resins for chips, connecting resins for electric cables, etc.

Furthermore, a very broad applicative field is that of coatings and paints in general, and in particular for printed circuits, magnetic tapes and discs, optical readout discs, optical fibers and optical systems in general, paints for aeronautical and space craft applications, barrier paints for marine environments, hydrophobic coatings for submarine systems, coatings of mechanical parts immersed in solvents and, in general, coatings of metallic systems subject to corrosion.

Unless otherwise specified in the examples, the properties of the materials are measured according to the following procedures:
glass transition=differential thermal analysis/heating, rate=16° C./minute,
dielectric constant (εr)/dissipation factor (Tg δ)=ASTM D 150/50 Hz/23° C.

EXAMPLE 1

22.0 g (0.10 moles) of pyromellitic anhydride in 200 ml of anhydrous acetone (distilled from pyromellitic anhydride) were charged into a 250 ml flask equipped with a cooler, a dropping funnel, and a thermometer. Under magnetic stirring, the solution was brought to boiling (T=59° C.), after which, in about two hours, a solution of 19.5 g (0.05 moles) of $C_6F_{12}(CH_2CH_2OH)_2$ in 30 ml of anhydrous acetone was added, so as to have always an excess of pryomellitic anhydride in order to prevent polymerization reactions.

On completion of the addition, the solution was further refluxed for 1 hour.

Now, by means of a Claisen distillation flask, acetone was exhaustively separated.

In the flask remained 41 g of a white powder which, on NMR $^{19}F$ and NMR $^{1}H$ analyses, was shown to be:

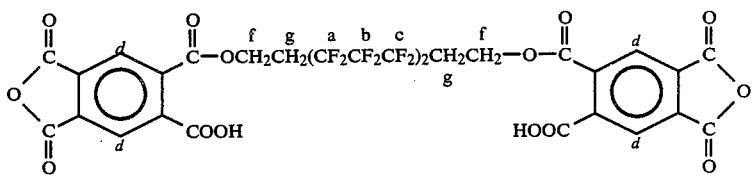

chemical shifts:
NMR $^{19}F$: (δ, $CFCl_3$) a=−113,
b=−121,
c=−123.
NMR$^1$ H: (67 , TMS) d=8.0–8.5,
f=4.7,
g=2.8.

In particular there was observed the disappearance of the signal at δ=3.9 corresponding to the methylene group in position with respect to the hydroxy group characteristic of the starting doil.

EXAMPLE 2

Following the procedure of Example 1 but using, as a fluoroalkane diol, 14.5 g (0.0050 moles) of $C_4F_8(CH_2CH_2OH)_2$, there were obtained 36 g of:

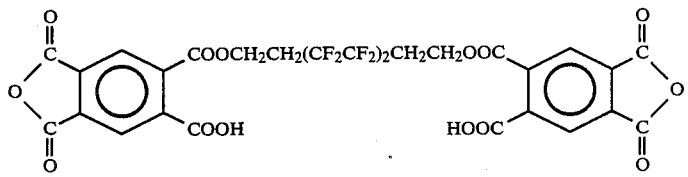

The structure was identified by IR and NMR analyses.

EXAMPLE 3

Following the procedure used in Example 1 but using, as fluoroalkane diols, 255 g (≃0.05 moles) of a mixture of $(8F_{16}(CH_2CH_2OH)_2$ (86%) and $C_{10}F_{20}(CH_2CH_2OH)_2$ (14%), there were obtained 47 g of:

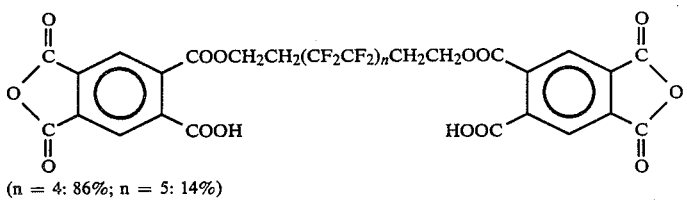

(n = 4: 86%; n = 5: 14%)

The structure was identified by IR and NMR analyses.

EXAMPLE 4

Into a 100 ml flask there were charged, in a nitrogen atmosphere, 10 g of 2,4-diisocyanatotoluene (0.057 moles) in 100 ml of diglyme and then, in 20 hours, a solution of 7.83 g of $C_4F_8(CH_2CH_2OH)_2$ (0.027 moles) in 10 ml of diglyme was added. The whole was heated to 80° C. and allowed to react for 2 hours under stirring, after which the reaction solvent was distilled off under reduced pressure. In this manner a white solid product (17.2 g) was obtained, the analysis (IR, NMR) of which was in accordance with the following structure:

| | |
|---|---|
| Glass transition temperature | = 156° C. |
| Dielectric constant ($\epsilon$ r) | = 3.2 |
| Water absorption | = 0.20% by weight after a 96-hour immersion at 100° C. |
| Contact angle ($H_2O$) | = 93°. |

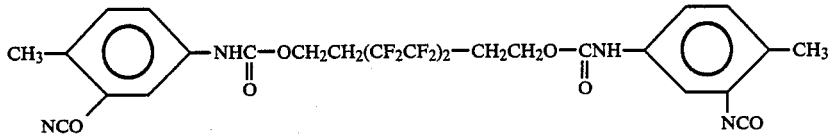

EXAMPLE 5

Analogously with what is described in Example 4, 12.25 g of isphorone diisocyanate (0.055 moles) were reacted with 8 g of $C_4F_8(CH_2CH_2OH)_2$ (0.027 moles) in diglyme.

Obtained were 20 g of a highly viscous, transparent liquid product, the chemical structure of which, confirmed by IR and NMR analyses, was the following:

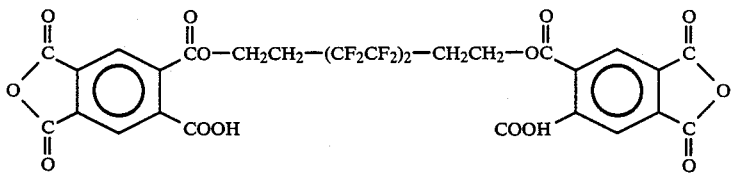

EXAMPLE 6

100 parts of a liquid epoxy resin based on bisphenol A - epichlorohydrin, having an epoxy equivalent weight=190, and 1 part of N-butyl imidazole were dissolved in acetone.

To this solution there was added an acetone solution of 90 parts of the fluorinated dianhydride:

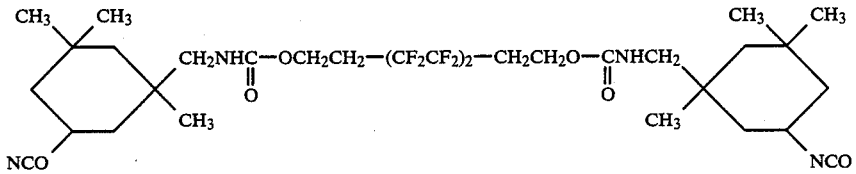

of Example 2 and 1 part of N-butyl imidazole.

The solvent was removed under vacuum and the mixture was cross-linked at 100° C. for 1 hour and at 165° C. for 8 hours.

The resulting resin was fully transparent, had a fluorine content equal to 10%, and exhibited the following properties:

EXAMPLE 7

100 parts of a liquid expoy resin based on bisphenol A- epichlorhydrin, having an epoxy equivalent weight equal to 190, were mixed with 56.5 parts of methylnadic anhydride, 33.5 parts of the fluorinated dianhydride:

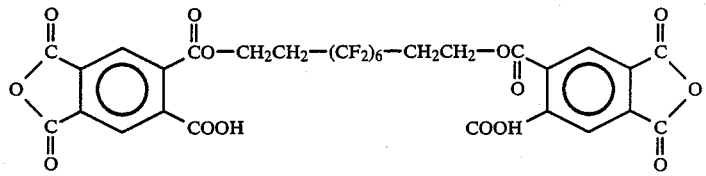

of Example 2 and 1 part of N-butyl imidazole.

After deaeration under vacuum, the mixture was crosslinked at 100° C. for 1 hour and at 165° C. for 6 hours.

The resulting resin was fully transparent, had a fluorine content equal to 5% by weight, and exhibited the following properties:

| | |
|---|---|
| Glass transition temperature | = 153° C. |
| Dielectric constant ($\epsilon$ r) | = 3.4 |
| Water absorption | = 0.35% by weight after a 96-hour immersion at 100° C. |
| Contact angle ($H_2O$) | = 87°. |

EXAMPLE 8 (comparative test)

The preceding example was repeated but using only methylnadic anhydride (90 parts by weight with respect to the bisphenol A - epichlorohydrin resin). The resulting resin had a dielectric constant=4, a water absorption=1.7% by weight under the same conditions, and a contact angle with water=62°.

EXAMPLE 9

25 parts by weight of a solid epoxy resin based on bisphenol A - epichlorohydrin having an epoxy equivalent weight=500 were dissolved by a heating in 80 parts by weight of acetone.

To this solution there was added 6.5 parts of hexamethylenediisocyanate and 1.7 parts of the fluorinated diisocyanate:

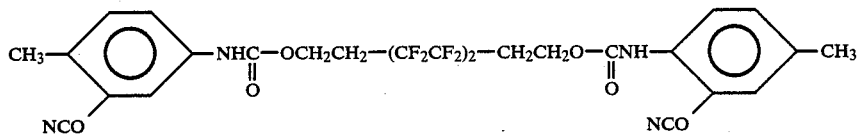

the preparation of which is described in Example 4.

Acetone was evaporated and 0.002 parts by weight of a 0.2 N solution of dibutyl tin acetate were added.

The mixture so obtained was homnogenized abed cross-linked at 100° C. for 6 hours.

The resulting resin had a fluorine content of 1.2% by weight and exhibited the following characteristics:

| | |
|---|---|
| Dielectric constant ($\epsilon$ r) = | 3.25 |
| Dissipation factor (Tg $\delta$) = | 0.008 |
| Contact angle (H$_2$O) = | 93°. |

EXAMPLE 10

Following the procedure of Example 9, a cross-linked epoxy resin was prepared starting from 20 parts of a solid epoxy resin having an epoxy equivalent weight=500, 7.8 parts of hexamethylenediisocyanate, and 2.1 parts of the fluorinated diisocyanate:

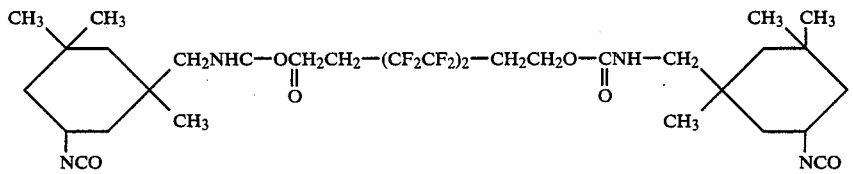

The resulting resin had a fluorine content equal to 1.1% by weight and the following charactersitics:

| | |
|---|---|
| Dielectric constant ($\epsilon$ r) = | 3.18 |
| Dissipation factor (Tg $\delta$) = | 0.007 |
| Contact angle (H$_2$O) = | 105°. |

EXAMPLE 11

By operating in like manner as in Example 10 but using a mixture of dissocyanates consisting of 5.8 parts of hexamethylene diisocyanate and of 4.4 parts of the fluorinated diisocyanate, a resin was obtained which had a fluorine content equal to 2.6 by weight and exhibited the following characteristics:

| | |
|---|---|
| Dielectric constant ($\epsilon$ r) = | 3.10 |
| Dissipation factor (Tg $\delta$) = | 0.0089 |
| Contact angle (H$_2$O) = | 124°. |

What is claimed is:

1. A process for cross-linking non-fluorinated epoxy resins, characterized in that, as cross-linking agents, perfluoroalkane compounds comprised in one of the following formulae are used:

$$A-(CF_2CF_2)_n A' \qquad (I)$$

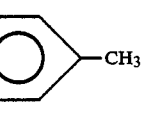

where:
n=2 to 8; m=1 to 8;, p=0 to 6; m+p being at least 2, A and A' are end groups containing in the aggregate two or more functional groups which are reactive with the starting epoxy resin and are selected from:
NH$_2$
COOH
OH
SH
NCO
an anhydride group.

2. The process of claim 1, wherein the nonfluorinated epoxy resins of known type may also contain hydroxyl groups.

3. The process of claim 1 or 2, wherein end groups A, A' consist of one or more functional groups, as defined in claim 1, linked to the perfluoroalkylene structure through a linking divalent aliphatic cycloaliphatic, aromatic or heterocyclic radical.

4. The process of claim 1 or 2, wherein the perfluoroalkane cross-linking agent is used in admixture with a non-fluorinated cross-linking agent.

5. Resins containing fluorine in an amount lower than 15% by weight, prepared from non-fluorinated epoxy resins by means of the cross-linking process as defined in claim 1 or 2.

6. Resins containing fluorine in an amount ranging from 1 to 5% by weight, prepared from non-fluorinated epoxy resins by means of the cross-linking process as defined in claim 1 or 2.

* * * * *